(12) United States Patent
Grond et al.

(10) Patent No.: US 11,518,777 B2
(45) Date of Patent: Dec. 6, 2022

(54) INHIBITORS OF THE SHIKIMATE PATHWAY

(71) Applicant: Eberhard Karls Universität Tübingen, Tübingen (DE)

(72) Inventors: Stephanie Grond, Tübingen-Hirschau (DE); Karl Forchhammer, Tübingen (DE); Klaus Brilisauer, Tübingen (DE)

(73) Assignee: Eberhard Karls Universität Tübingen, Tübingen (DE)

( * ) Notice: Subject to any disclaimer, the term of this patent is extended or adjusted under 35 U.S.C. 154(b) by 4 days.

(21) Appl. No.: 16/766,610

(22) PCT Filed: Nov. 23, 2018

(86) PCT No.: PCT/EP2018/082400
§ 371 (c)(1),
(2) Date: May 22, 2020

(87) PCT Pub. No.: WO2019/101937
PCT Pub. Date: May 31, 2019

(65) Prior Publication Data
US 2020/0385416 A1     Dec. 10, 2020

(30) Foreign Application Priority Data
Nov. 24, 2017    (DE) .................. 10 2017 010 898.6

(51) Int. Cl.
| | |
|---|---|
| *A01N 43/08* | (2006.01) |
| *A01N 43/90* | (2006.01) |
| *A61K 31/70* | (2006.01) |
| *C07H 7/02* | (2006.01) |
| *C07H 9/02* | (2006.01) |

(52) U.S. Cl.
CPC .............. *C07H 7/02* (2013.01); *A01N 43/08* (2013.01); *A01N 43/90* (2013.01); *A61K 31/70* (2013.01); *C07H 9/02* (2013.01)

(58) Field of Classification Search
None
See application file for complete search history.

(56) References Cited

U.S. PATENT DOCUMENTS

2015/0141357 A1    5/2015    Wang et al.

FOREIGN PATENT DOCUMENTS

| | | | |
|---|---|---|---|
| WO | WO-2012016935 A1 * | 2/2012 | ............... C07H 3/00 |
| WO | 2019101937 A3 | 8/2019 | |

OTHER PUBLICATIONS

Wolff, Manfred E. "Burger's Medicinal Chemistry, 5ed, Part I", John Wiley & Sons, 1995, pp. 975-977 (Year: 1995).*
Banker, G.S. et al, "Modern Pharmaceutics, 3ed.", Marcel Dekker, New York, 1996, p. 596 (Year: 1996).*
Hricovíniová, Zuzana. "Isomerization as a route to rare ketoses: the beneficial effect of microwave irradiation on Mo (VI)-catalyzed stereospecific rearrangement." Tetrahedron: Asymmetry 19.2 (2008): 204-208 (5 pages).
Ito et al., "Structure of SF-666 A and SF-666 B, New Monosaccharides", Research Laboratories, Meiji Seika Kaisha Ltd., Morooka, Yokohama, (Japan) (accepted for publication, Nov. 29, 1970).
Tzin et al, "Shikimate Pathway and Aromatic Amino Acid Biosynthesis", Plant Biology Division, The Samuel Roberts Noble Foundation, Ardmore, Oklahoma,Online posting date: Aug. 15, 2012.
Montchamp et al., "Diastereoselection and in vivo inhibition of 3-dehydroquinate synthase", J. Am. Chem. Soc. 1992, 114, 12, 4453-4459.
Tian et al., "Inhibitor Ionization as a Determinant of Binding to 3-Dehydroquinate Synthase", J. Org. Chem. 1996, 61, 21, 7373-7381.
Duke et al., "Glyphosate: a once-in-a-century herbicide", Pest Manag Sci . Apr. 2008;64(4):319-25. doi: 10.1002/ps.1518 . . . .
Gijsen et al., "Sequential Three- and Four-Substrate Aldol Reactions Catalyzed by Aldolases", J. Am. Chem. Soc. 1995, 117, 29, 7585-7591.
Martin et al., "Fluorination or hydroxylation of non activated C?H bonds in amides and ketones using CCI4 or NBS in superacids", Tetrahedron Letters, vol. 37, Issue 17, Apr. 22, 1996, pp. 2967-2970.
Drueckhammer et al, "Reversible and in situ formation of organic arsenates and vanadates as organic phosphate mimics in enzymatic reactions: mechanistic investigation of aldol reactions and synthetic applications", J. Org. Chem. 1989, 54, 1, 70-77.
T. Shomura et al., "New Antibodiotics, SF-666A and B. II. Biological characteristics of SF-666A and B", XP-002789121 (Feb. 19, 2019).

* cited by examiner

*Primary Examiner* — Traviss C McIntosh, III
(74) *Attorney, Agent, or Firm* — Fox Rothschild LLP

(57) ABSTRACT

The present invention relates to novel inhibitors of the shikimate pathway (shikimic acid pathway), pharmaceutical compositions comprising these novel inhibitors, methods for the production of the inhibitors and their use as antibiotics and herbicides.

10 Claims, 2 Drawing Sheets

INHIBITORS OF THE SHIKIMATE PATHWAY

CROSS-REFERENCES TO RELATED APPLICATIONS

This application is a 35 U.S.C. § 371 U.S. national entry of International Application No. PCT/EP2018/082400, having an International filing date of Nov. 23, 2018 which claims under 35 U.S.C. § 119 the benefit of German Application 10 2017 010898.6 filed on Nov. 24, 2017. The entire contents of these applications are incorporated herein by reference in their entirety.

The present invention relates to novel inhibitors of the shikimate pathway (shikimic acid pathway), pharmaceutical compositions comprising these novel inhibitors, methods for the production of the inhibitors and their use as antibiotics and herbicides.

The shikimate pathway is a metabolic route used e.g. by bacteria, fungi, algae, some protozoan parasites and plants for the biosynthesis of aromatic compounds such as folates and aromatic amino acids. This pathway is not found in humans or animals.

The seven enzymes involved in the shikimate pathway are DAHP (3-deoxy-D-arabinoheptulosonate-7-phosphate) synthase, 3-dehydroquinate synthase, 3-dehydroquinate dehydratase, shikimate dehydrogenase, shikimate kinase, EPSP synthase, and chorismate synthase. The pathway starts with two substrates, phosphoenol pyruvate and erythrose-4-phosphate and ends with chorismate, a substrate for the three aromatic amino acids. The fifth enzyme involved is the shikimate kinase, an enzyme that catalyzes the ATP-dependent phosphorylation of shikimate to form shikimate 3-phosphate. Shikimate 3-phosphate is then coupled with phosphoenol pyruvate to give 5-enolpyruvylshikimate-3-phosphate via the enzyme 5-enolpyruvylshikimate-3-phosphate (EPSP) synthase.

In recent times the need for new herbicides has risen which are non-detrimental for the surroundings and especially for humans and animals.

It is known to use Glyphosate as an herbicide. It blocks 5-enolpyruvylshikimat-3-phosphat-synthase (EPSPS), the sixth enzyme of the shikimate pathway. However, there is an increasing disquiet that glyphosate might be cancerogenic and might harm plants and animals. Therefore, a need exists to provide novel herbicides, which are not cancerogenic or detrimental in any other way to human beings and are not harmful for useful plants and animals.

In order to overcome the above problems, the present invention provides a compound of formula (I)

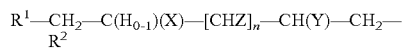

wherein

R$^1$ is H, F, NH$_2$, OH, Cl, or Br

R$^2$ is H, F, Cl, Br, NH$_2$, CH$_3$, COOH, CH$_2$OH, CH$_2$F, CH$_2$Br, CH$_2$Cl, CH$_2$NH$_2$, CH$_2$—CH$_2$F, CH$_2$—CH$_2$Cl, CH$_2$—CH$_2$Br, CH$_2$—CH$_2$NH$_2$, CH$_2$—CH$_3$, CH$_2$—COOH, or CH$_2$—CH$_2$OH n=3

X is O, NH, Cl, Br, OPO$_3$, or OSO$_3$,

Y is OH, or NH$_2$, each Z is independently H, F, OH, NH$_2$, Cl, or Br, wherein each OH group independently of each other can be substituted by a group of the formula COCH$_3$, COCH$_2$CH$_3$, COCH$_2$CH$_2$CH$_3$, CO(C$_6$H$_5$), COCH$_2$ (C$_6$H$_5$), OPO$_3$, OSO$_3$, and wherein two neighboring OH groups independently of each other can be linked with a group of the formula —C(CH$_3$)$_2$— or a cyclic form thereof, and a stereoisomer, salt, prodrug, ester, acetal and/or tautomeric form thereof.

These compounds are useful inhibitors of an enzyme involved in the shikimate pathway. They are highly specific and already highly effective in small doses without any side effects for humans or animals.

FIGURES

Figure 1A:
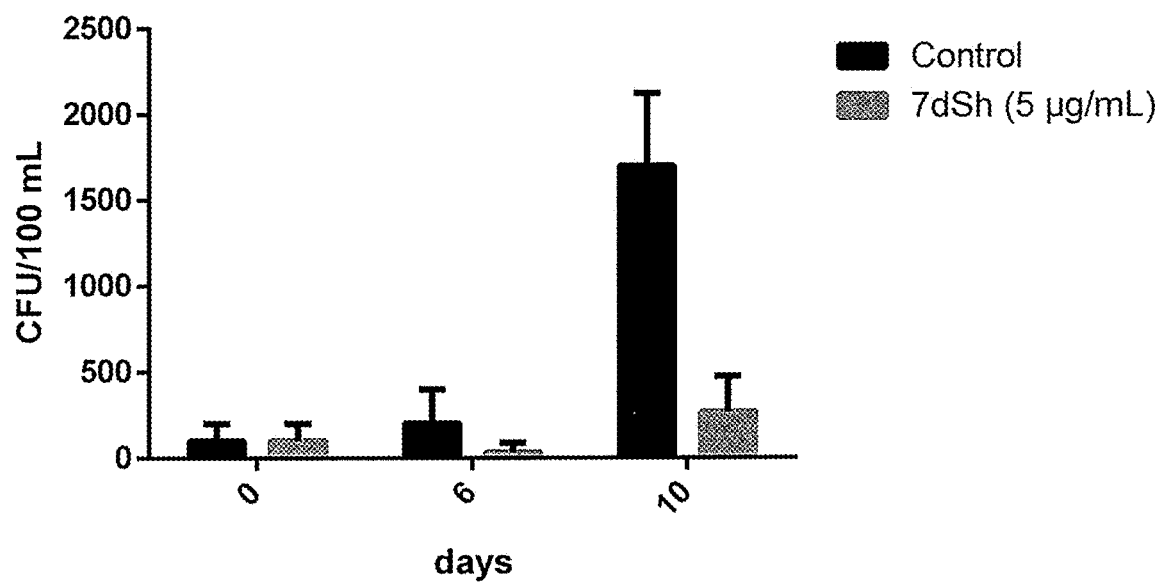
FIG. 1a shows the CFUs of *Legionella* in the presence of 7dSh and an untreated control.

Compounds are generally described herein using standard nomenclature. For compounds having asymmetric centers, it should be understood that, unless otherwise specified, all of the optical isomers and mixtures thereof are encompassed. Compounds with two or more asymmetric elements can also be present as mixtures of diastereomers. In addition, compounds with carbon-carbon double bonds may occur in Z- and E-forms, with all isomeric forms of the compounds being included in the present invention unless otherwise specified. Where a compound exists in various tautomeric forms, a recited compound is not limited to any one specific tautomer, but rather is intended to encompass all tautomeric forms. Recited compounds are further intended to encompass compounds in which one or more atoms are replaced with an isotope, i.e., an atom having the same atomic number but a different mass number. By way of general example, and without limitation, isotopes of hydrogen include tritium and deuterium and isotopes of carbon include $^{11}$C, $^{13}$C, and $^{14}$C.

Compounds according to the formulas provided herein, which have one or more stereogenic center(s), have an enantiomeric excess of at least 50%. For example, such compounds may have an enantiomeric excess of at least 60%, 70%, 80%, 85%, 90%, 95%, or 98%. Some embodiments of the compounds have an enantiomeric excess of at least 99%. It will be apparent that single enantiomers (optically active forms) can be obtained by asymmetric synthesis, synthesis from optically pure precursors or by resolution of the racemates. Resolution of the racemates can be accomplished, for example, by conventional methods such as crystallization in the presence of a resolving agent, or chromatography, using, for example, a chiral HPLC column.

Compounds herein may also be described using a general formula that includes variables such as, e.g., A, R$^1$-R$^4$, Y, etc. Unless otherwise specified, each variable within such a formula is defined independently of any other variable, and any variable that occurs more than one time in a formula is defined independently at each occurrence. Thus, for example, if a group is shown to be substituted with 0-2 R*, the group may be unsubstituted or substituted with up to two R* groups and R* at each occurrence is selected independently from the definition of R*. Also, combinations of substituents and/or variables are permissible only if such combinations result in stable compounds, i.e., compounds that can be isolated, characterized and tested for biological activity.

According to an embodiment, naturally occurring compounds of formula I as such are excluded from the scope of the present invention. According to a further embodiment 7-deoxy-2-heptulose as such is excluded from the scope of the present invention. However, the inventive use of this compound is comprised within the scope of the present invention.

A "pharmaceutically acceptable salt" of a compound disclosed herein preferably is an acid or base salt that is generally considered in the art to be suitable for use in contact with the tissues of human beings or animals without excessive toxicity or carcinogenicity, and preferably without irritation, allergic response, or other problem or complication. Such salts include mineral and organic acid salts of basic residues such as amines, as well as alkali or organic salts of acidic residues such as carboxylic acids.

Suitable pharmaceutical salts include, but are not limited to, salts of acids such as hydrochloric, phosphoric, hydrobromic, malic, glycolic, fumaric, sulfuric, sulfamic, sulfanilic, formic, toluenesulfonic, methanesulfonic, benzene sulfonic, ethane disulfonic, 2-hydroxyethylsulfonic, nitric, benzoic, 2-acetoxybenzoic, citric, tartaric, lactic, stearic, salicylic, glutamic, ascorbic, pamoic, succinic, fumaric, maleic, propionic, hydroxymaleic, hydroiodic, phenylacetic, alkanoic such as acetic, HOOC—$(CH_2)_n$—COOH where n is any integer from 0 to 4, i.e., 0, 1, 2, 3, or 4, and the like. Similarly, pharmaceutically acceptable cations include, but are not limited to sodium, potassium, calcium, aluminum, lithium and ammonium. Those of ordinary skill in the art will recognize further pharmaceutically acceptable salts for the compounds provided herein. In general, a pharmaceutically acceptable acid or base salt can be synthesized from a parent compound that contains a basic or acidic moiety by any conventional chemical method. Briefly, such salts can be prepared by reacting the free acid or base forms of these compounds with a stoichiometric amount of the appropriate base or acid in water or in an organic solvent, or in a mixture of the two. Generally, the use of nonaqueous media, such as ether, ethyl acetate, ethanol, isopropanol or acetonitrile, is preferred.

It will be apparent that each compound of formula (I) may, but need not, be present as a hydrate, solvate or non-covalent complex. In addition, the various crystal forms and polymorphs are within the scope of the present invention, as are prodrugs of the compounds of formula (I) provided herein.

A "prodrug" is a compound that may not fully satisfy the structural requirements of the compounds provided herein, but is modified in vivo, following administration to a subject or patient, to produce a compound of formula (I) provided herein. For example, a prodrug may be an acylated derivative of a compound as provided herein. Prodrugs include compounds wherein hydroxy, carboxy, amine or sulfhydryl groups are bonded to any group that, when administered to a mammalian subject, cleaves to form a free hydroxy, carboxy, amino, or sulfhydryl group, respectively. Examples of prodrugs include, but are not limited to, acetate, formate, phosphate and benzoate derivatives of alcohol and amine functional groups within the compounds provided herein. Prodrugs of the compounds provided herein may be prepared by modifying functional groups present in the compounds in such a way that the modifications are cleaved in vivo to generate the parent compounds.

A "substituent," as used herein, refers to a molecular moiety that is covalently bonded to an atom within a molecule of interest, e.g. to a compound of formula (I) or a prodrug thereof. For example, a "ring substituent" may be a moiety such as a halogen, alkyl group, haloalkyl group or other substituent described herein that is covalently bonded to an atom, preferably a carbon or nitrogen atom, that is a ring member. The term "substituted," as used herein, means that any one or more hydrogens on the designated atom is replaced with a selection from the indicated substituents, provided that the designated atom's normal valence is not exceeded, and that the substitution results in a stable compound, i.e., a compound that can be isolated, characterized and tested for biological activity. When a substituent is oxo, i.e., =O, then 2 hydrogens on the atom are replaced. An oxo group that is a substituent of an aromatic carbon atom results in a conversion of —CH— to —C(=O)— and a loss of aromaticity. For example, a pyridyl group substituted by oxo is a pyridone.

As used herein, a wording defining the limits of a range of length such as, e. g., "from 1 to 5" means any integer from 1 to 5, i.e. 1, 2, 3, 4 and 5. In other words, any range defined by two integers explicitly mentioned is meant to comprise and disclose any integer defining said limits and any integer comprised in said range.

In the shikimate pathway, DAHP (3-deoxy-D-arabinoheptulosonate-7-phosphate) is the natural substrate of DHQS (3-dehydroquinate synthase). DAHP has a chain length of seven carbon atoms which is required for the conversion with DHQS.

Thus, a compound according to the present invention having a chain length of seven C-atoms is especially preferred as an inhibitor of DHQS since it closely conforms to the steric requirements (like the binding site) of that enzyme.

7dSh and other 7-deoxy-ketoses can be present in any tautomeric form (keto-enol-aldehyde form), in their pyranose or furanose form or as a hydrate.

Examples of preferred forms are:

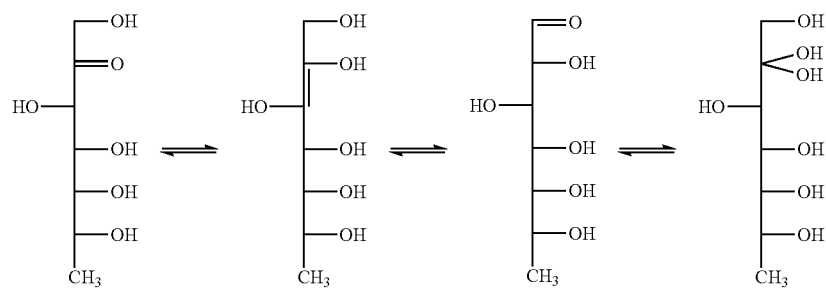

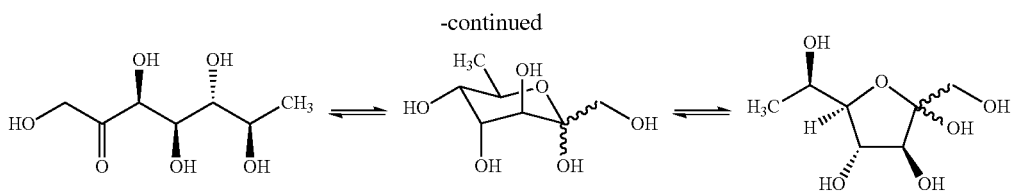

The compounds according to the present invention may also have a chain length of eight or nine carbon atoms, thus forming octulose and nonulose derivatives. Thereby the specificity of the inhibitor can be regulated according to specific use. The increased chain length confers the derivatives a higher stability against enzymatic digestion and metabolization. Introduction of saturated hydrocarbons furthermore lowers the polarity of the metabolites.

Further preferred are compounds of formula (I) wherein each Z is OH.

Also preferred are compounds of formula (I) wherein $R^1$ is OH. Further preferred are compounds of formula (I) wherein $R^2$ is H.

Moreover, preferred are compounds of formula (I) wherein X is O.

Further preferred are compounds of formula (I) wherein Y is OH.

Further preferred are compounds of formula (I) wherein $R^1$ is H, or F.

Also preferred are compounds of formula (I) wherein $R^2$ is COOH, F, $NH_2$, $CH_3$, or $CH_2OH$.

Further preferred are compounds of formula (I) wherein 1-3, preferably 2 or 3, especially preferred 3 substituents Z are independently of each other H, F, OH, or $NH_2$.

Further preferred are compounds of formula (I) wherein each Z independently of each other is H, $OCOCH_3$, $OCOCH_2CH_3$, $OCOCH_2CH_2CH_3$, $OCO(C_6H_5)$ or $OCOCH_2(C_6H_5)$.

Further preferred are prodrugs of the compounds of the present invention. Examples of prodrugs are compounds according to the present invention, which have been esterified, with groups like acetyl, propionyl, butyryl, benzoyl, or benzyl groups. These ester groups can be cleaved off in vivo.

Especially preferred are compounds of formula (I)

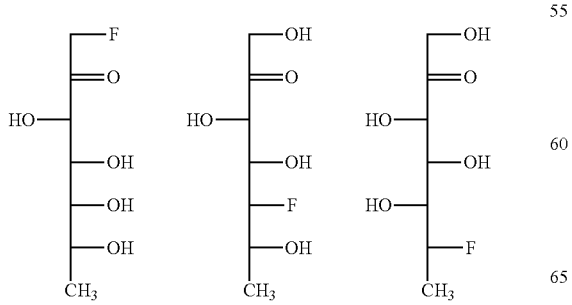

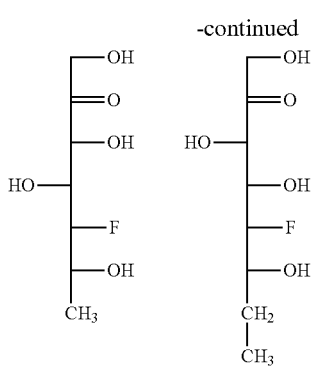

Especially preferred are groups of formula (I) wherein F-atoms are bonded to the $C_1$, $C_3$, $C_4$, and/or $C_6$ atom.

Especially preferred are compounds of formula (I) having the following formulae:

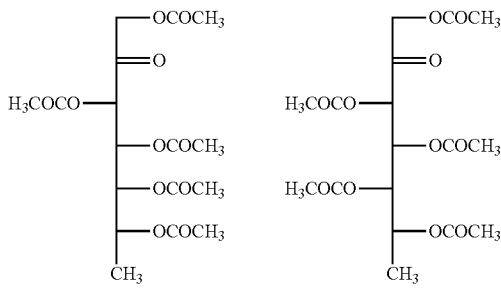

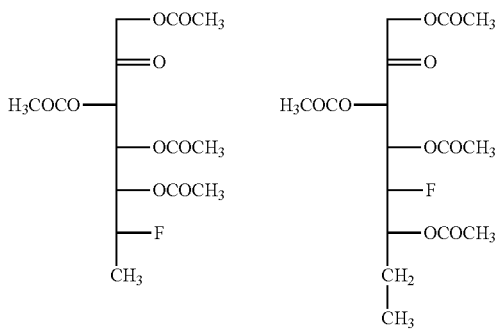

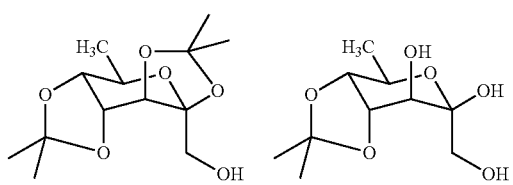

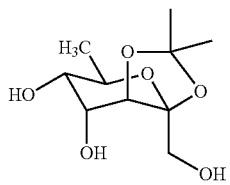

Especially preferred are compounds of formula (I) wherein n=3, $R^1$ is H, F, or OH, X is O, $NH_2$, or Cl, Y is OH, $NH_2$, Z is OH, F or $NH_2$, and $R^2$ is H, or a salt, prodrug or tautomeric form thereof, which can be protected by a protecting group, e.g. $OCOCH_3$, $OCOCH_2CH_3$, $OCOCH_2CH_2CH_3$, $OCO(C_6H_5)$ or $OCOCH_2(C_6H_5)$, and wherein two neighboring OH groups independently of each other can be linked with a group of the formula —$C(CH_3)_2$—.

Naturally occurring 7dSh can be present as a six-membered ring (pyranose form) with an oxygen atom (Y=OH) being part of the ring. By replacing the oxygen (Y=OH) atom with another heteroatom (Y=NH or SH), the six membered ring will have the corresponding other heteroatom at its binding site. Thereby the specificity of the inhibitor can be regulated according to specific requests. Introduction of heteroatoms and the halogenation of the monosaccharides increases the stability against degradation. Thereby a more persistent effect on targeted organisms is achieved.

The compounds of the present invention may have any configuration and all these configurations are comprised within the scope of the present invention.

7-deoxy-heptuloses can have any one of the following configurations:

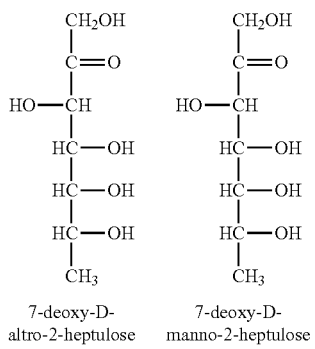

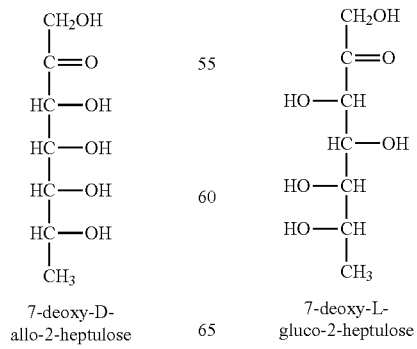

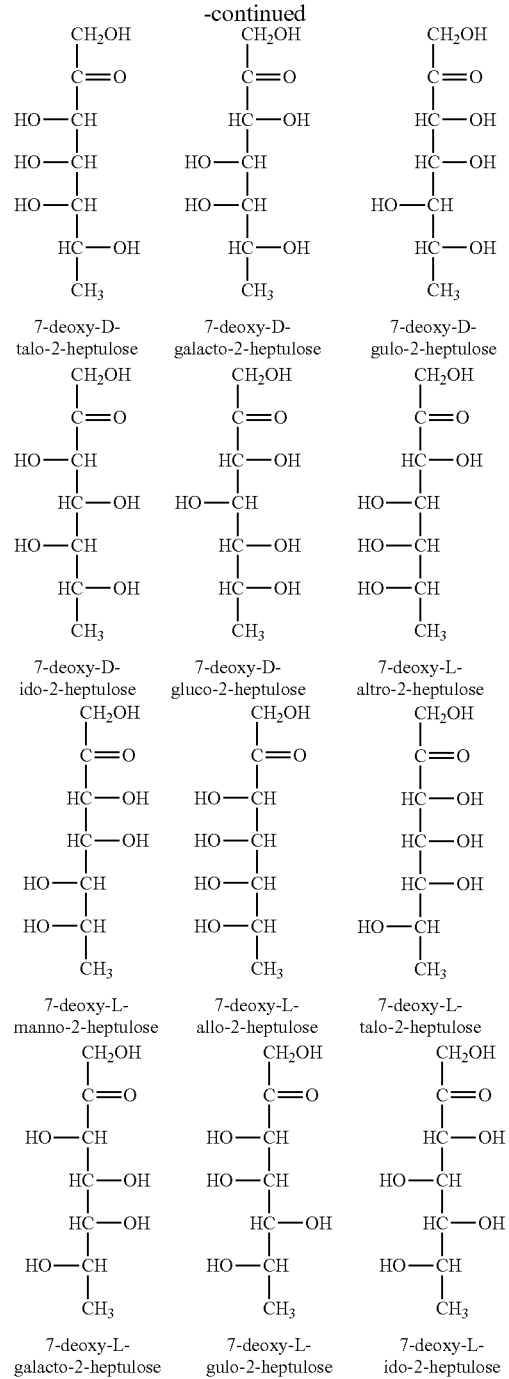

The naturally occurring 7-deoxy sedoheptulose has the D-altro configuration. Preferably, this compound as such is not included within the scope of the present invention. However, the inventive use of this compound is comprised within the scope of the present invention.

Preferred are compounds of formula (I) wherein the stereocenters at C3-C6 have the inverted stereoconfiguration of the natural 7-deoxy sedoheptulose. This compound is 7-deoxy-L-al-tro-2-heptulose.

Moreover preferred are compounds of formula (I) wherein one stereocenter at C3-C6 can have inverted stereoconfiguration of the natural 7-deoxy sedoheptulose (epimers of 7dSh) as well as their enantiomers. Examples of these are 7-deoxy-D-manno-2-heptulose, 7-deoxy-L-galacto-2-heptulose, 7-deoxy-L-allo-2-heptulose, 7-deoxy-D-ido-2-heptulose.

Moreover preferred are compounds of formula (I) wherein two of the stereocenters at C3-C5 each independently can have the inverted stereoconfiguration of the natural 7-deoxy sedoheptulose as well as their enantiomers. Examples of these are 7-deoxy-D-gluco-2-heptulose, 7-deoxy-L-gluco-2-heptulose, 7-deoxy-D-gulo-2-heptulose, 7-deoxy-D-talo-2-heptulose By modifying the stereochemical configuration of the compounds according to the present invention, it is possible to flexibly address the specific need of inhibition according to the actual use.

The therapeutic use of compounds of formula (I), their pharmacologically acceptable salts, prodrugs, solvates and hydrates and also formulations and pharmaceutical compositions containing the same are within the scope of the present invention. The present invention also relates to the use of those compounds etc. of formula (I) as active ingredients in the preparation or manufacture of a medicament, especially, the use of compounds of formula (I), their pharmacologically acceptable salts, prodrugs or solvates and hydrates and also formulations and pharmaceutical compositions for the treatment of infections as well as their use for the preparation of medicaments for the treatment of infections.

The present invention furthermore refers to the use of a compound or a pharmaceutical composition according to the present invention for the inhibition of 3-dehydroquinate synthase.

The pharmaceutical compositions according to the present invention comprise at least one compound of formula (I) and, optionally, one or more carrier substances, excipients and/or adjuvants. Pharmaceutical compositions may additionally comprise, for example, one or more of water, buffers such as, e.g., neutral buffered saline or phosphate buffered saline, ethanol, mineral oil, vegetable oil, dimethylsulfoxide, carbohydrates such as e.g., glucose, mannose, sucrose or dextrans, mannitol, adjuvants, antioxidants, chelating agents such as EDTA or glutathione and/or preservatives. Furthermore, one or more other active ingredients may, but need not, be included in the pharmaceutical compositions provided herein. For instance, the compounds of the invention may advantageously be employed in combination with another antibiotic, an anti-fungal, or anti-viral agent, an-anti histamine, a non-steroidal anti-inflammatory drug, a disease modifying anti-rheumatic drug, a cytostatic drug, a drug with smooth muscle activity modulatory activity or mixtures of the aforementioned.

Pharmaceutical compositions may be formulated for any appropriate route of administration, including, for example, topical such as, e.g., transdermal or ocular, oral, buccal, nasal, vaginal, rectal or parenteral administration. The term parenteral as used herein includes subcutaneous, intradermal, intravascular such as, e.g., intravenous, intramuscular, spinal, intracranial, intrathecal, intraocular, periocular, intraorbital, intrasynovial and intraperitoneal injection, as well as any similar injection or infusion technique. In certain embodiments, compositions in a form suitable for oral use are preferred. Such forms include, for example, tablets, troches, lozenges, aqueous or oily suspensions, dispersible powders or granules, emulsion, hard or soft capsules, or syrups or elixirs. Within yet other embodiments, compositions provided herein may be formulated as a lyophilizate.

Compositions intended for oral use may further comprise one or more components such as sweetening agents, flavoring agents, coloring agents and/or preserving agents in order to provide appealing and palatable preparations. Tablets contain the active ingredient in admixture with physiologically acceptable excipients that are suitable for the manufacture of tablets. Such excipients include, for example, inert diluents such as, e.g., calcium carbonate, sodium carbonate, lactose, calcium phosphate or sodium phosphate, granulating and disintegrating agents such as, e.g., corn starch or alginic acid, binding agents such as, e.g., starch, gelatin or acacia, and lubricating agents such as, e.g., magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed.

Formulations for oral use may also be presented as hard gelatin capsules wherein the active ingredient is mixed with an inert solid diluent such as, e.g., calcium carbonate, calcium phosphate or kaolin, or as soft gelatin capsules wherein the active ingredient is mixed with water or an oil medium such as, e.g., peanut oil, liquid paraffin or olive oil.

Aqueous suspensions may contain the active ingredient(s) in admixture with excipients suitable for the manufacture of aqueous suspensions. Such excipients include suspending agents such as, e.g., sodium carboxymethylcellulose, methylcellulose, hydropropylmethylcellulose, sodium alginate, polyvinylpyrrolidone, gum tragacanth and gum acacia; and dispersing or wetting agents such as, e.g., naturally-occurring phosphatides such as lecithin, condensation products of an alkylene oxide with fatty acids such as polyoxyethylene stearate, condensation products of ethylene oxide with long chain aliphatic alcohols such as heptadecaethyleneoxycetanol, condensation products of ethylene oxide with partial esters derived from fatty acids and a hexitol such as polyoxyethylene sorbitol monooleate, or condensation products of ethylene oxide with partial esters derived from fatty acids and hexitol anhydrides such as polyethylene sorbitan monooleate. Aqueous suspensions may also comprise one or more preservatives, for example ethyl, or n-propyl p-hydroxybenzoate, one or more coloring agents, one or more flavoring agents, and one or more sweetening agents, such as sucrose or saccharin.

Oily suspensions may be formulated by suspending the active ingredients in a vegetable oil such as, e.g., arachis oil, olive oil, sesame oil or coconut oil, or in a mineral oil such as liquid paraffin. The oily suspensions may contain a thickening agent such as beeswax, hard paraffin or cetyl alcohol. Sweetening agents such as those set forth above, and/or flavoring agents may be added to provide palatable oral preparations. Such suspensions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, such as sweetening, flavoring and coloring agents, may also be present.

Pharmaceutical compositions may also be in the form of oil-in-water emulsions. The oily phase may be a vegetable oil such as, e.g., olive oil or arachis oil, a mineral oil such as, e.g., liquid paraffin, or a mixture thereof. Suitable emulsifying agents include naturally-occurring gums such as, e.g., gum acacia or gum tragacanth, naturally-occurring phosphatides such as, e.g., soy bean lecithin, and esters or partial esters derived from fatty acids and hexitol, anhydrides such as, e.g., sorbitan monooleate, and condensation products of partial esters derived from fatty acids and hexitol with ethylene oxide such as, e.g., polyoxyethylene sorbitan monooleate. An emulsion may also comprise one or more sweetening and/or flavoring agents.

Syrups and elixirs may be formulated with sweetening agents, such as glycerol, propylene glycol, sorbitol or sucrose. Such formulations may also comprise one or more demulcents, preservatives, flavoring agents and/or coloring agents.

Compounds may be formulated for local or topical administration, such as for topical application to the skin or mucous membranes, such as in the eye. Formulations for topical administration typically comprise a topical vehicle combined with active agent(s), with or without additional optional components. Suitable topical vehicles and additional components are well known in the art, and it will be apparent that the choice of a vehicle will depend on the particular physical form and mode of delivery. Topical vehicles include water; organic solvents such as alcohols such as, e.g., ethanol or isopropyl alcohol or glycerin; glycols such as, e.g., butylene, isoprene or propylene glycol; aliphatic alcohols such as, e.g., lanolin; mixtures of water and organic solvents and mixtures of organic solvents such as alcohol and glycerin; lipid-based materials such as fatty acids, acylglycerols including oils, such as, e.g., mineral oil, and fats of natural or synthetic origin, phosphoglycerides, sphingolipids and waxes; protein-based materials such as collagen and gelatin; silicone-based materials, both non-volatile and volatile; and hydrocarbon-based materials such as microsponges and polymer matrices. A composition may further include one or more components adapted to improve the stability or effectiveness of the applied formulation, such as stabilizing agents, suspending agents, emulsifying agents, viscosity adjusters, gelling agents, preservatives, antioxidants, skin penetration enhancers, moisturizers and sustained release materials. Examples of such components are described in Martindale—The Extra Pharmacopoeia (Pharmaceutical Press, London 1993) and Martin (ed.), Remington's Pharmaceutical Sciences. Formulations may comprise microcapsules, such as hydroxymethylcellulose or gelatin-microcapsules, liposomes, albumin microspheres, micro-emulsions, nanoparticles or nanocapsules.

A topical formulation may be prepared in a variety of physical forms including, for example, solids, pastes, creams, foams, lotions, gels, powders, aqueous liquids, emulsions, sprays and skin patches. The physical appearance and viscosity of such forms can be governed by the presence and amount of emulsifier(s) and viscosity adjuster(s) present in the formulation. Solids are generally firm and non-pourable and commonly are formulated as bars or sticks, or in particulate form; solids can be opaque or transparent, and optionally can contain solvents, emulsifiers, moisturizers, emollients, fragrances, dyes/colorants, preservatives and other active ingredients that increase or enhance the efficacy of the final product. Creams and lotions are often similar to one another, differing mainly in their viscosity; both lotions and creams may be opaque, translucent or clear and often contain emulsifiers, solvents, and viscosity adjusting agents, as well as moisturizers, emollients, fragrances, dyes/colorants, preservatives and other active ingredients that increase or enhance the efficacy of the final product. Gels can be prepared with a range of viscosities, from thick or high viscosity to thin or low viscosity. These formulations, like those of lotions and creams, may also contain solvents, emulsifiers, moisturizers, emollients, fragrances, dyes/colorants, preservatives and other active ingredients that increase or enhance the efficacy of the final product. Liquids are thinner than creams, lotions, or gels and often do not contain emulsifiers. Liquid topical products often contain solvents, emulsifiers, moisturizers, emollients, fragrances, dyes/colorants, preservatives and other active ingredients that increase or enhance the efficacy of the final product.

Suitable emulsifiers for use in topical formulations include, but are not limited to, ionic emulsifiers, cetearyl alcohol, non-ionic emulsifiers like polyoxyethylene oleyl ether, PEG-40 stearate, ceteareth-12, ceteareth-20, ceteareth-30, ceteareth alcohol, PEG-100 stearate and glyceryl stearate. Suitable viscosity adjusting agents include, but are not limited to, protective colloids or non-ionic gums such as hydroxyethylcellulose, xanthan gum, magnesium aluminum silicate, silica, microcrystalline wax, beeswax, paraffin, and cetyl palmitate. A gel composition may be formed by the addition of a gelling agent such as chitosan, methyl cellulose, ethyl cellulose, polyvinyl alcohol, polyquaterniums, hydroxyethylcellulose, hydroxypropylcellulose, hydroxypropylmethylcellulose, carbomer or ammoniated glycyrrhizinate. Suitable surfactants include, but are not limited to, nonionic, amphoteric, ionic and anionic surfactants. For example, one or more of dimethicone copolyol, polysorbate 20, polysorbate 40, polysorbate 60, polysorbate 80, lauramide DEA, cocamide DEA, and cocamide MEA, oleyl beta-ine, cocamidopropyl phosphatidyl PG-dimonium chloride, and ammonium laureth sulfate may be used within topical formulations.

Suitable preservatives include, but are not limited to, anti-microbials such as methylparaben, propylparaben, sorbic acid, benzoic acid, and formaldehyde, as well as physical stabilizers and antioxidants such as vitamin E, sodium ascorbate/ascorbic acid and propyl gallate. Suitable moisturizers include, but are not limited to, lactic acid and other hydroxy acids and their salts, glycerin, propylene glycol, and butylene glycol. Suitable emollients include lanolin alcohol, lanolin, lanolin derivatives, cholesterol, petrolatum, isostearyl neopentanoate and mineral oils. Suitable fragrances and colors include, but are not limited to, FD&C Red No. 40 and FD&C Yellow No. 5. Other suitable additional ingredients that may be included in a topical formulation include, but are not limited to, abrasives, absorbents, anti-caking agents, anti-foaming agents, anti-static agents, astringents such as, e.g., witch hazel, alcohol and herbal extracts such as chamomile extract, binders/excipients, buffering agents, chelating agents, film forming agents, conditioning agents, propellants, opacifying agents, pH adjusters and protectants.

An example of a suitable topical vehicle for formulation of a gel is: hydroxypropylcellulose (2.1%); 70/30 isopropyl alcohol/water (90.9%); propylene glycol (5.1%); and Polysorbate 80 (1.9%). An example of a suitable topical vehicle for formulation as a foam is: cetyl alcohol (1.1%); stearyl alcohol (0.5%); Quaternium 52 (1.0%); propylene glycol (2.0%); Ethanol 95 PGF3 (61.05%); deionized water (30.05%); P75 hydrocarbon propellant (4.30%). All percents are by weight.

Typical modes of delivery for topical compositions include application using the fingers; application using a physical applicator such as a cloth, tissue, swab, stick or brush; spraying including mist, aerosol or foam spraying; dropper application; sprinkling; soaking; and rinsing. Controlled release vehicles can also be used, and compositions may be formulated for transdermal administration as a transdermal patch.

A pharmaceutical composition may be formulated as inhaled formulations, including sprays, mists, or aerosols. Such formulations are particularly useful for the treatment of asthma or other respiratory conditions. For inhalation formulations, the compounds provided herein may be delivered via any inhalation methods known to those skilled in the art. Such inhalation methods and devices include, but are not limited to, metered dose inhalers with propellants such as CFC or HFA or propellants that are physiologically and environmentally acceptable. Other suitable devices are breath operated inhalers, multidose dry powder inhalers and aerosol nebulizers. Aerosol formulations for use in the subject method typically include propellants, surfactants and co-solvents and may be filled into conventional aerosol containers that are closed by a suitable metering valve.

Inhalant compositions may comprise liquid or powdered compositions containing the active ingredient that are suitable for nebulization and intrabronchial use, or aerosol compositions administered via an aerosol unit dispensing metered doses. Suitable liquid compositions comprise the active ingredient in an aqueous, pharmaceutically acceptable inhalant solvent, e.g., isotonic saline or bacteriostatic water. The solutions are administered by means of a pump or squeeze-actuated nebulized spray dispenser, or by any other conventional means for causing or enabling the requisite dosage amount of the liquid composition to be inhaled into the patient's lungs. Suitable formulations, wherein the carrier is a liquid, for administration, as for example, a nasal spray or as nasal drops, include aqueous or oily solutions of the active ingredient.

Formulations or compositions suitable for nasal administration, wherein the carrier is a solid, include a coarse powder having a particle size, for example, in the range of 20 to 500 microns which is administered in the manner in which snuff is administered, i.e., by rapid inhalation through the nasal passage from a container of the powder held close up to the nose. Suitable powder compositions include, by way of illustration, powdered preparations of the active ingredient thoroughly intermixed with lactose or other inert powders acceptable for intrabronchial administration. The powder compositions can be administered via an aerosol dispenser or encased in a breakable capsule which may be inserted by the patient into a device that punctures the capsule and blows the powder out in a steady stream suitable for inhalation.

Pharmaceutical compositions may also be prepared in the form of suppositories such as e.g., for rectal administration. Such compositions can be prepared by mixing the drug with a suitable non-irritating excipient that is solid at ordinary temperatures but liquid at the rectal temperature and will therefore melt in the rectum to release the drug. Suitable excipients include, for example, cocoa butter and polyethylene glycols.

Pharmaceutical compositions may be formulated as sustained release formulations such as, i.e., a formulation such as a capsule that creates a slow release of modulator following administration. Such formulations may generally be prepared using well known technology and administered by, for example, oral, rectal or subcutaneous implantation, or by implantation at the desired target site. Carriers for use within such formulations are biocompatible, and may also be biodegradable; preferably the formulation provides a relatively constant level of modulator release. The amount of modulator contained within a sustained release formulation depends upon, for example, the site of implantation, the rate and expected duration of release and the nature of the condition to be treated or prevented.

For the treatment of infections, the dose of the biologically active compound according to the invention may vary within wide limits and may be adjusted to individual requirements. Active compounds according to the present invention are generally administered in a therapeutically effective amount. Preferred doses range from about 0.1 mg to about 140 mg per kilogram of body weight per day, about 0.5 mg to about 7 g per patient per day. The daily dose may be administered as a single dose or in a plurality of doses. The amount of active ingredient that may be combined with the carrier materials to produce a single dosage form will vary depending upon the host treated and the particular mode of administration. Dosage unit forms will generally contain between from about 1 mg to about 500 mg of an active ingredient.

It will be understood, however, that the specific dose level for any particular patient will depend upon a variety of factors including the activity of the specific compound employed, the age, body weight, general health, sex, diet, time of administration, route of administration, and rate of excretion, drug combination, i.e. other drugs being used to treat the patient, and the severity of the particular disease undergoing therapy.

Preferred compounds of the invention will have certain pharmacological properties. Such properties include, but are not limited to oral bioavailability, such that the preferred oral dosage forms discussed above can provide therapeutically effective levels of the compound in vivo.

The compounds and pharmaceutical compositions according to the present invention can be administered to a patient such as, e.g., a human, orally or topically, and are present within at least one body fluid or tissue of the patient. Accordingly, the present invention further provides methods for treating patients suffering from an infection. As used herein, the term "treatment" encompasses both disease-modifying treatment and symptomatic treatment, either of which may be prophylactic, i.e., before the onset of symptoms, in order to prevent, delay or reduce the severity of symptoms, or therapeutic, i.e., after the onset of symptoms, in order to reduce the severity and/or duration of symptoms. Patients may include but are not limited to primates, especially humans, domesticated companion animals such as dogs, cats, horses, and livestock such as cattle, pigs, sheep, with dosages as described herein.

It is also within the present invention that the compounds according to the invention are used as or for the manufacture of a diagnostic agent, whereby such diagnostic agent is for the diagnosis of the diseases and conditions which can be addressed by the compounds of the present invention for therapeutic purposes as disclosed herein.

For various applications, the compounds of the invention can be labelled by isotopes, fluorescence or luminescence markers, antibodies or antibody fragments, any other affinity label like nanobodies, aptamers, peptides etc., enzymes or enzyme substrates. The labelled compounds according to the present invention may be used in therapy, diagnosis and other applications such as research tools in vivo and in vitro, in particular the applications disclosed herein.

The compounds and pharmaceutical compositions according to the present invention are preferably administered in a minimal medium, that is, a medium containing mainly inorganic salts and water.

In addition, the compounds and pharmaceutical compositions according to the present invention are especially suited to inhibit the growth of organisms being able to grow in minimal media. Examples thereof are Cyanobacteriae, *Escherichia coli, Proteus vulgaris, Bacillus cereus, Serratia marcescens, Pseudomonas putida, Pseudomonas aeruginosa* and related ubiquitous bacteria. Compounds and pharmaceutical compositions according to the present invention can especially be used for the treatment of infections of the urinary tract.

The compounds according to the present invention can be used to inhibit the growth of organisms having the shikimate pathway.

The present invention furthermore refers to the use of a compound according to the present invention for the inhibition of the growth of bacteriae, especially prototrophic bacteriae. Especially useful is the use of the compounds of the present invention for the inhibition of growth of cyanobacteriae.

The present invention furthermore refers to the use of a compound according to the present invention for the inhibition of the growth of *Legionella*. *Legionella* is a pathogenic group of Gram-negative bacteria that includes the species *L. pneumophila*. It can be found in many environments including soil and aquatic systems; upon inhalation *Legionella* can cause Legionnaires disease, a potentially lethal disease. An inhibition of the growth of *Legionella* can, for example, be achieved when adding a compound according to the present invention to an aquatic system, infested with *Legionella*.

It is preferred to use concentrations of 5 μg/mL and more, especially of 10 μg/mL to 100 μg/mL. Thereby the number of CFUs can be reduced to ¼ (see FIG. 1a).

In complex media, final products of the shikimate pathway are comprised, which can be metabolized by the respective bacteriae etc., thereby counteracting the inhibition, provided by the compounds of the present invention.

The present invention furthermore refers to the use of a compound according to the present invention as a herbicide.

The present invention furthermore refers to the use of a compound according to the present invention as a non-selective herbicide also called total weedkiller.

The compounds of the present invention exhibit their herbicidal activity already in small amounts, e.g. 26 μM to 350 μM, preferably 50 μM to 700 μM, especially preferred in the range 100 μM to 260 μM. Thus, the compounds of the present invention have a significantly higher activity than the known herbicide glyphosate, see FIG. 2.

The present invention also refers to the use of a compound according to the present invention as a fungicide.

The present invention furthermore refers to the use of a compound according to the present invention as an algicide.

It also refers to the use of the novel inhibitors for the inhibition of the formation of biofilms.

7dSh and other 7-deoxy-ketoses can be used as preserving agents and replace parabens and other supplemented preservatives. The 7-deoxy-ketoses can inhibit the growth of bacteria in various applications.

Synthesis of the Inventive Compounds

The present invention, furthermore refers to the synthesis of 7-deoxy-sedoheptulose and its derivatives.

According to the present invention, 5-deoxy-D-ribose is reacted with beta-hydroxypyruvate. The reaction is catalyzed by a transketolase, which has been obtained from *E. coli*, and the temperature is set to its optimal temperature (about 30° C.). Preferably, a buffer like HEPES is used. The products obtained may be purified by using size-exclusion chromatography, medium-pressure chromatography and HPLC.

Further compounds according to the present invention can be produced by using corresponding alternative educts and reacting them with further enzymes like aldolases.

EXAMPLES

Chemoenzymatic Synthesis of 7dSh with Transketolase

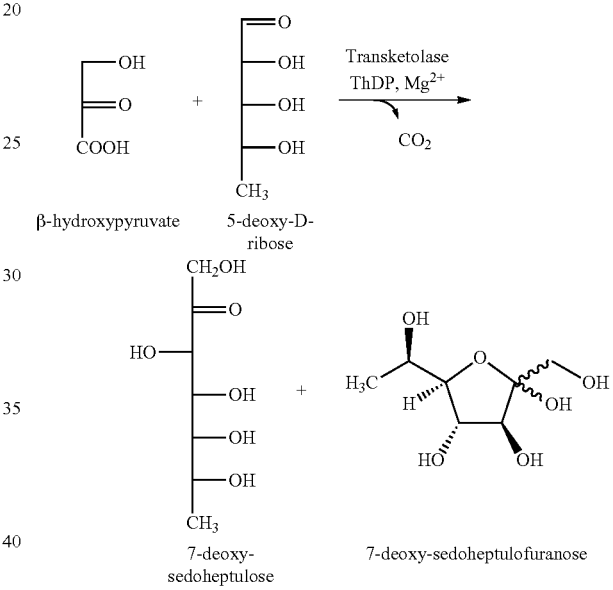

5-Deoxy-D-ribose (Glentham Life Sciences) (50 mg, 250 mM) was dissolved in 1.5 mL HEPES buffer (100 mM, pH=7.5) containing thiamine pyrophosphate (1.3 mg, 2 mM) and $MgCl_2$ (0.4 mg, 3 mM). 3-hydroxypyruvate as its lithium salt hydrate (54 mg, 285 mM) was added and the pH adjusted to pH=7.5. The reaction was initiated by addition of 4 mg transketolase (EC 2.2.1.1) and shaken at 400 rpm and 30° C. for 24 h (Thriller®, Peqlab). The reaction was stopped by the addition of 6 mL MeOH followed by a centrifugation (2500 rpm, 10 min). Supernatant was evaporated and purified by bioactivity guided purification via size-exclusion chromatography (SEC) on Sephadex LH20, medium pressure liquid chromatography (MPLC) on normal phase and ligand/ion-exchange high-performance liquid chromatography (HPLC), coupled with an evaporative light scattering detector (ELSD), finally led to a chromatographically pure compound.

The transketolase exhibits a wide substrate specificity. Therefore, the use of alternative deoxy acceptor substrates (fluorinated/amino/deoxy C5-aldoses) for the transketolase reaction results in the generation of alternative monosaccharides with 7-deoxy function (fluorinated/amino/deoxy C7-ketoses). Depicted below are selected products resulting from the variation of acceptor substrate:

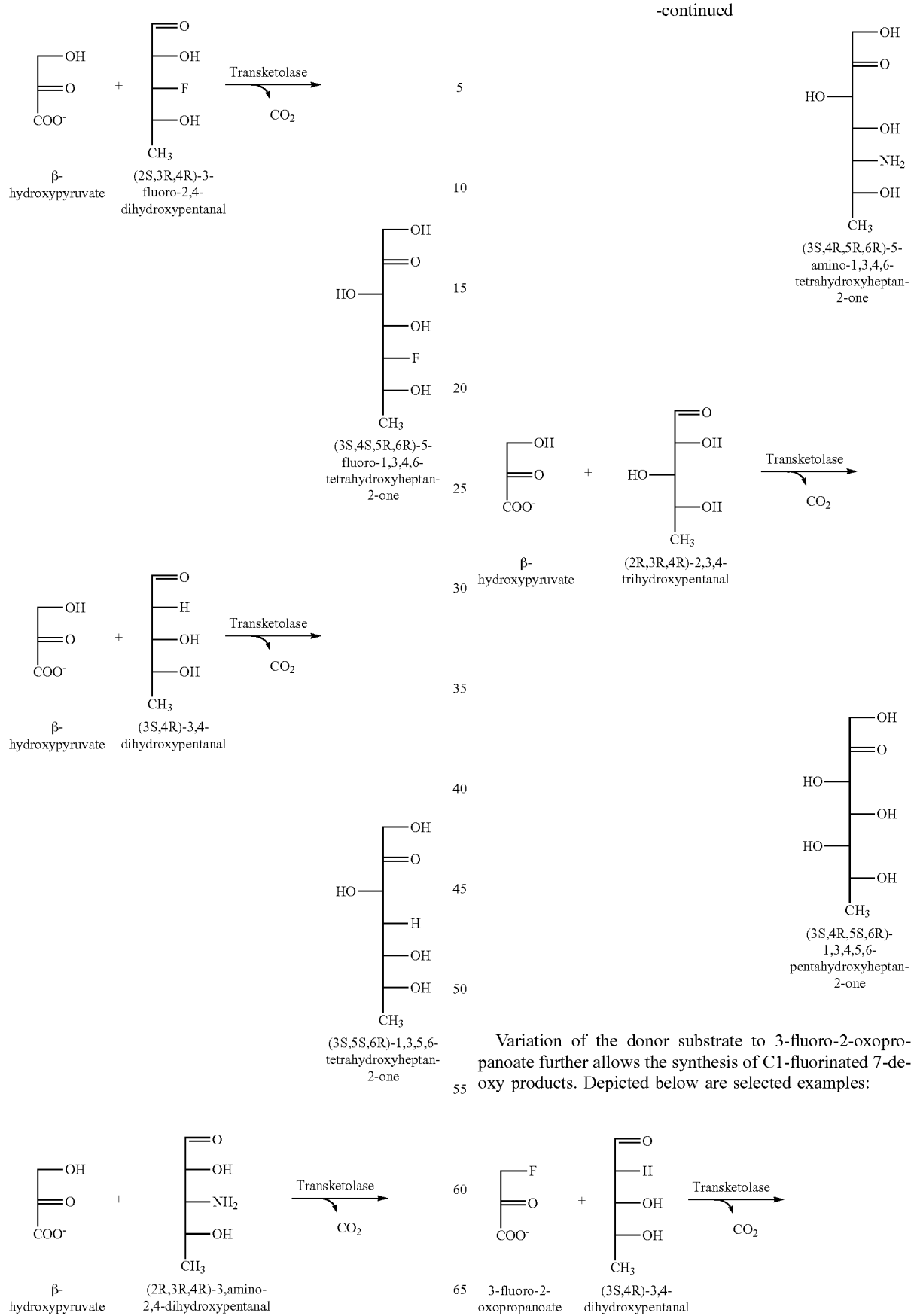
Variation of the donor substrate to 3-fluoro-2-oxopropanoate further allows the synthesis of C1-fluorinated 7-deoxy products. Depicted below are selected examples:

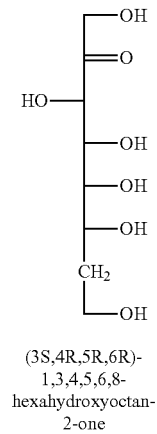

(3S,5S,6R)-1-fluoro-3,5,6-trihydroxyheptan-2-one

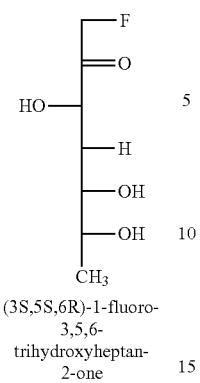

(3S,4R,5R,6R)-1,3,4,5,6,8-hexahydroxyoctan-2-one

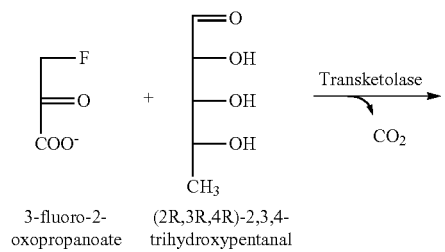

3-fluoro-2-oxopropanoate + (2R,3R,4R)-2,3,4-trihydroxypentanal

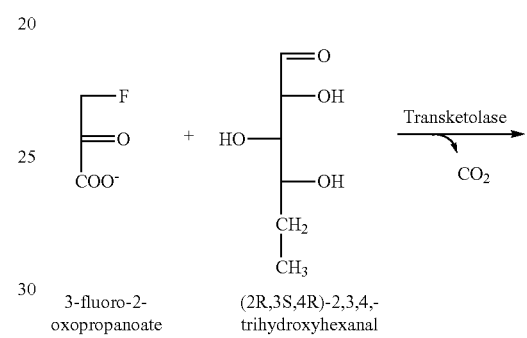

3-fluoro-2-oxopropanoate + (2R,3S,4R)-2,3,4,-trihydroxyhexanal

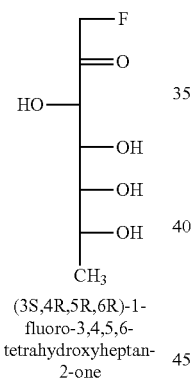

(3S,4R,5R,6R)-1-fluoro-3,4,5,6-tetrahydroxyheptan-2-one (3S,4R,5S,6R)-1-fluoro-3,4,5,6-tetrahydroxyoctan-2-one The use of C6 and C7 aldoses furthermore allows the generation of C8 and C9 7-deoxy monosaccharides. Depicted below are selected examples:

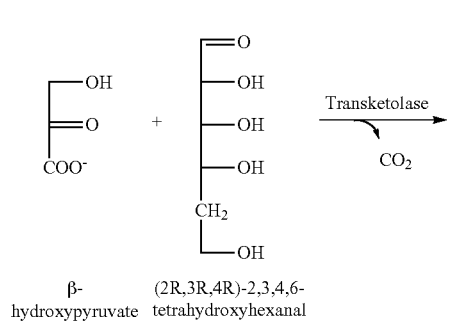

β-hydroxypyruvate + (2R,3R,4R)-2,3,4,6-tetrahydroxyhexanal

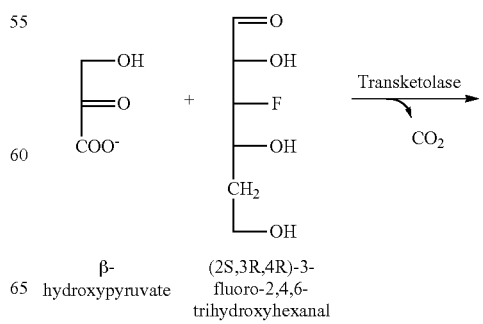

β-hydroxypyruvate + (2S,3R,4R)-3-fluoro-2,4,6-trihydroxyhexanal

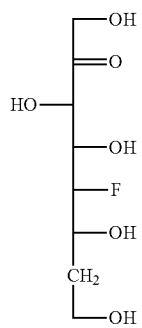

(3S,4S,5R,6R)-5-fluoro-1,3,4,6,8-pentahydroxyoctan-2-one

Chemoenzymatic Synthesis of 7-deoxymonosaccharides with Aldolases

The generation of the C7-C9 7-deoxy sugars can also be achieved by the utilization of aldolases. The aldolases use DAHP as the donor substrate and transfer the C3 unit to many acceptor substrates. Depicted below is the synthesis of 7-deoxy-gluco-2-heptulose:

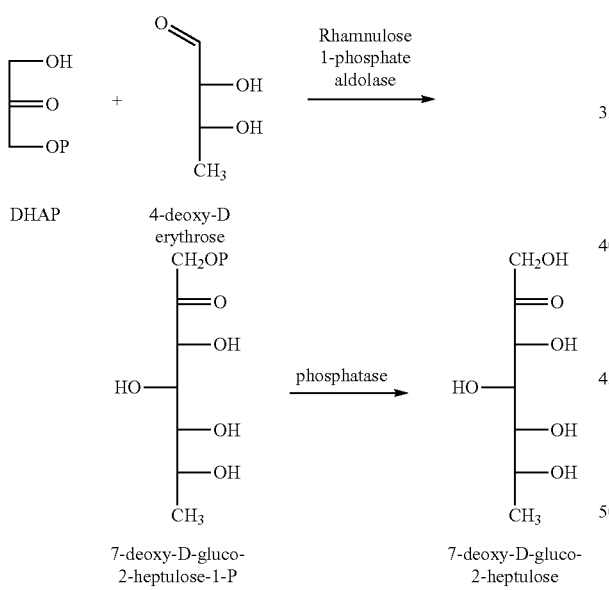

An aqueous solution (1 mL) of DHAP (0.15 mM) and 4-deoxy-D-erythrose (0.12 mM) is adjusted to pH 6.9 with 1 M NaOH. Subsequent, rhamnulose-1-phosphate aldolase (2 U/mL) is added and shaken at 400 rpm and 25° C. for 24 h. The reaction is stopped by the addition of 2 mL MeOH followed by a centrifugation (2500 rpm, 10 min). The pH of the supernatant is adjusted to 2.5. Acid phosphatase (orthophosphoric monoesterphosphohydrolase, EC 3.1.3.2) is added (1 U/mL) and incubated at 37° C. for 6 h. Reaction is stopped by adding 2 mL 0.1 NaOH and 4 mL MeOH followed by a centrifugation (2500 rpm, 10 min). Supernatant is evaporated and purified via size-exclusion chromatography (SEC) on Sephadex LH20, medium pressure liquid chromatography (MPLC) on normal phase and ligand/ion-exchange high-performance liquid chromatography (HPLC), coupled with an evaporative light scattering detector (ELSD). Purification finally results in the chromatographically pure compound.

The aldolase exhibits a wide substrate specificity. Therefore, the use of alternative deoxy acceptor substrates (fluorinated/amino/deoxy C4-aldoses) for the transketolase reaction results in the generation of alternative monosaccharides with 7-deoxy function (fluorinated/amino/deoxy C7-ketoses). Depicted below are selected products resulting from the variation of acceptor substrate:

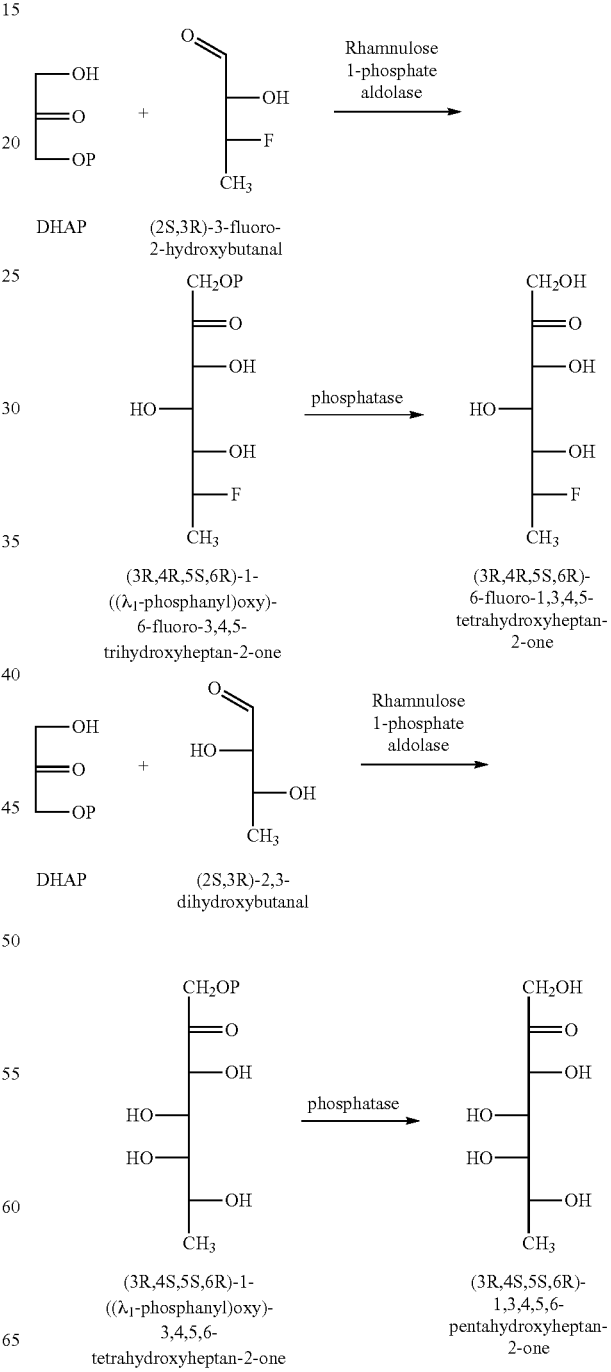

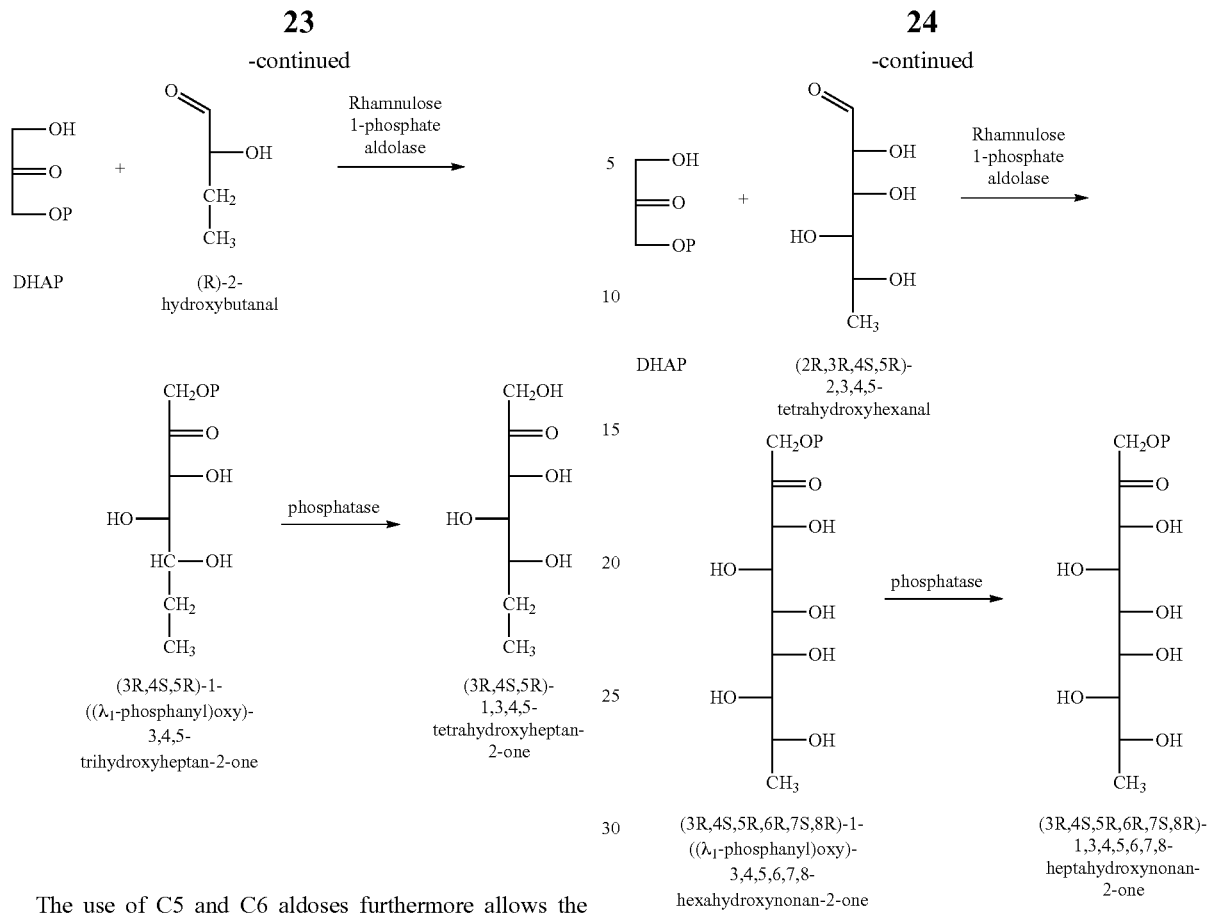
The use of C5 and C6 aldoses furthermore allows the generation of C8 and C9 7-deoxy monosaccharides. Depicted below are selected examples:
The utilization of other DAHP dependent aldolases further allows the generation of other stereo-configurations at C3 and C4. Depicted below are selected products resulting from the variation of aldolases:
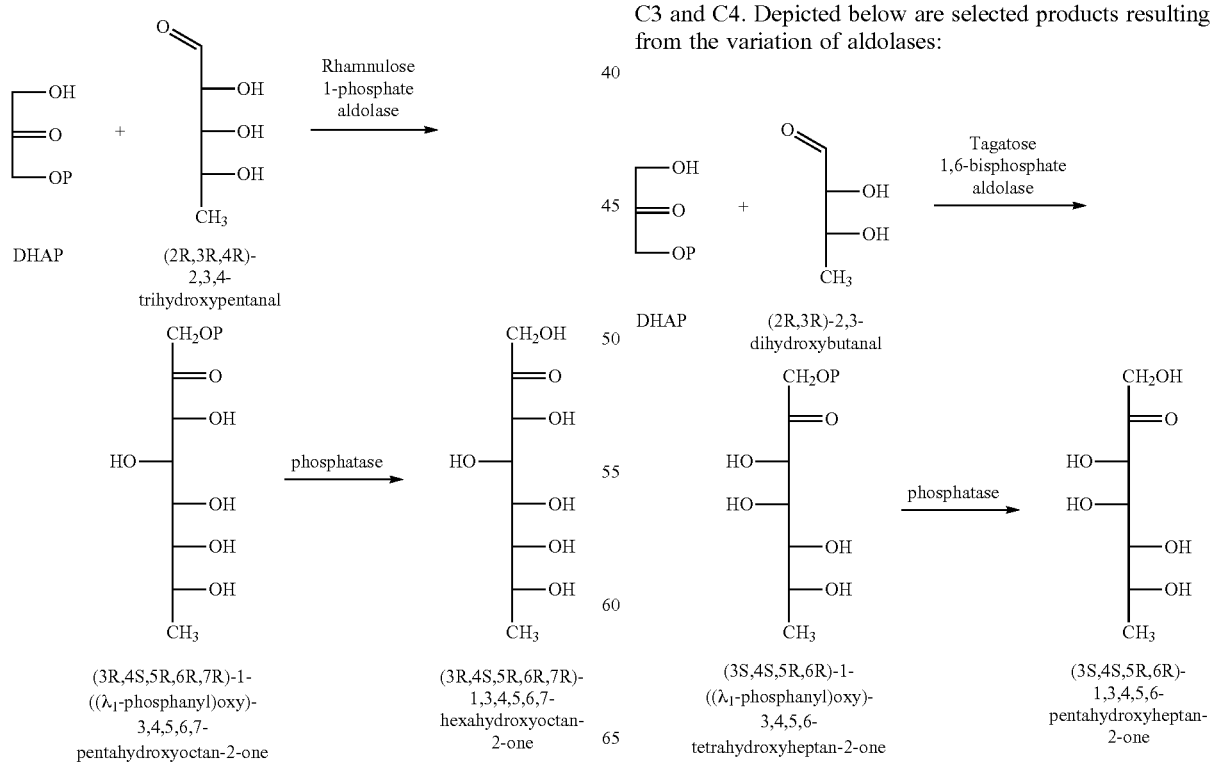

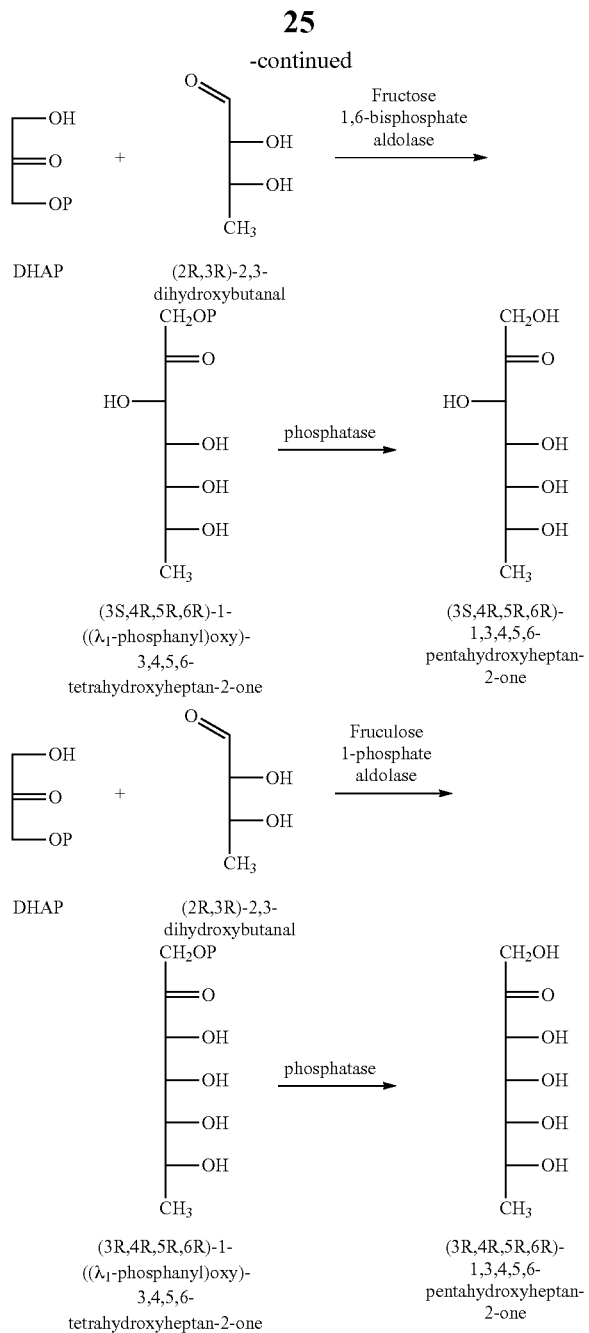

-continued

DHAP (2R,3R)-2,3-dihydroxybutanal (3S,4R,5R,6R)-1-((λ1-phosphanyl)oxy)-3,4,5,6-tetrahydroxyheptan-2-one (3S,4R,5R,6R)-1,3,4,5,6-pentahydroxyheptan-2-one

DHAP (2R,3R)-2,3-dihydroxybutanal (3R,4R,5R,6R)-1-((λ1-phosphanyl)oxy)-3,4,5,6-tetrahydroxyheptan-2-one (3R,4R,5R,6R)-1,3,4,5,6-pentahydroxyheptan-2-one

Chemical Derivatization of 7dSh and Other 7-deoxy-ketoses a) Semisynthesis of penta-O-acetyl-7-deoxy-D-altro-heptulose (Equals to Peracetylated 7dSh)

A suspension of anhydrous sodium acetate (15 mg (0.18 mmol)) and 1.7 mL (1.8 g, 18 mmol) of acetic acid is gently heated in a 50 mL-round-bottomed flask with cooling condenser. After removing the heating, 34.9 mg 7-deoxy-D-altro-heptulose (0.18 mmol) are added stepwise and the mixture continues to reflux while heating again for an hour, according to reaction monitoring by TLC until reaction is complete. Then, the reaction mixture is slowly poured on ice and stirred until the ice is melted or 2 hours. Filtration or lyophilization gives a the yellowish solid. The product can be recrystallized from 2 mL ethanol or purified by preparative HPLC (C18 column, solvent MeOH:H2O, solvents evaporated in vacuo).

b) Semisynthesis of O-propionylated 7-deoxy-D-altro-heptulose

Evaporated 7-deoxy-D-altro-heptulose samples is dissolved in 50 microL of pyridine, and 100 microL of propionic anhydride is added to obtain the respective esters. After 45 min of incubation at 60° C., samples are evaporated to dryness. Dissolved in 100 microL diethylether, ethyl acetate or dichloromethane the product is purified by preparative HPLC (C18 column, solvent MeOH:H2O, solvents evaporated in vacuo)

c) Semisynthesis of Benzyolated 7-deoxy-D-altro-heptulose 7-deoxy-D-altro-heptulose (30 mg, 0.15 mmol) is dissolved in 50 microL of dry pyridine, benzoyl chloride (211 mg, 174 microL, which equals to 2 equivalents per OH-group) is added and the mixture is stirred at room temperature for 2 hours or until the reaction is complete (monitoring by TLC). With vigorous stirring, water is added, and the solution is extracted 3 times with dichloromethane (alternatively diethylether, ethyl acetate). The combined organic phases are lyophilized and preparative HPLC yields the pure benzoylated product (C18 column, solvent MeOH:H2O, solvents evaporated in vacuo).

d) Semisynthesis of Acetonide 7-deoxy-D-altro-heptulose

A two-neck 50 mL flask with DMF (2 mL) was sealed with a septum for reaction monitoring and degassed with argon for 10 min. Acetonide formation was achieved at room temperature by addition of the 7-deoxy-D-altro-heptulose (30 mg, 0.15 mmol) 2,2-dimethoxypropane (47 mg, 0.45 mmol) and p-toluensulfonic acid (p-TSA, 26 mg, 0.15 mmol). The reaction mixture was stirred at room temperature for 5-10 hours. Water (10 mL) was added, the product was extracted with ice cold ethyl acetate (3×10 mL) and the solvent was removed in vacuo. The reaction product was purified by column chromatography using a preparative HPLC C18 column and solvent MeOH:$H_2O$ to give the acetonide a colorless oil.

Activity Against *Legionella*

Water samples were obtained from a little used water tap in a laboratory of the working group Forchhammer, Eberhard Karls University of Tübingen. The water samples (800 mL) were incubated for 10 days in 1 L screw neck bottles at 37° C. CFUs of *Legionella* were determined on solid agar plates.

FIG. 1*a* shows the CFUs of *Legionella* in natural water samples incubated in the presence of 7dSh and a control for 10 days. CFUs were determined in two biological replicates for the untreated control and three biological replicates for the 7dSh treatment.

As can be taken from this figure, the number of CFUs was 4-5 times lower after ten days in the presence of 7dSh when compared to the control.

Thereby, it has clearly been shown that the compounds of the present invention have a pronounced effect on the inhibition of prokaryotes.

Activity Against Fungi

Suppressive Effects of 7dSh on *S. cerevisiae*

Yeast nitrogen base media without amino acids (Sigma-Aldrich) was sterilized and then supplemented with 0.5 g/L fructose and 1 g/L casamino acids. 10 mL cultures of *Saccharomyces cerevisiae* were grown in 50 mL Erlenmeyer flasks under continuous shaking (120 rpm) at 30° C. for 48 h.

One sample was treated with 50 µM 7dSh (10 µg/mL). Another sample was treated with the 11-fold amount of glyphosate. The $OD_{600}$ of the cultures (initial $OD_{600}$=0.05) was determined in a Specord 205 (Analytik Jena).

Figure 1B:
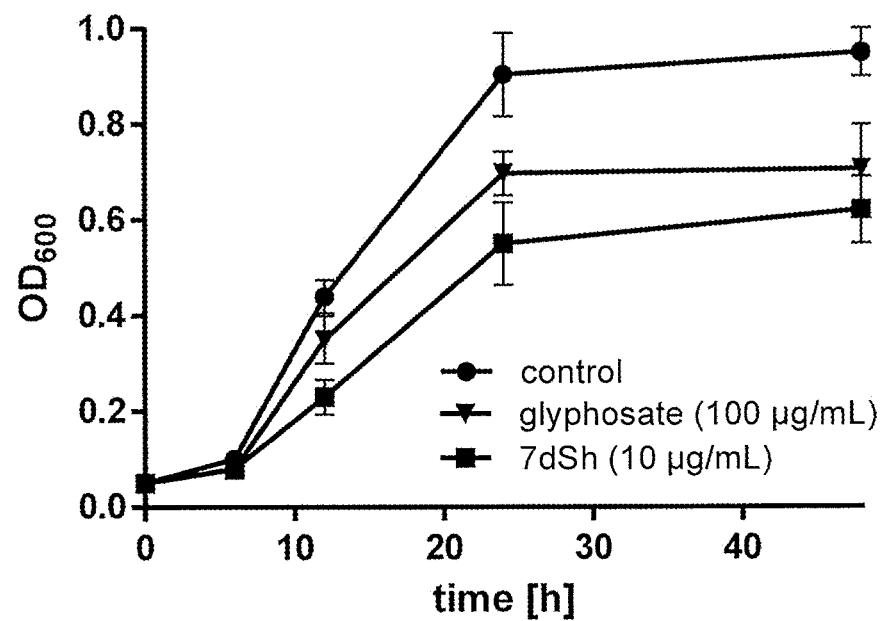
FIG. 1b shows the optical density of *S. cerevisiae* grown in the presence of a control, glyphosate and 7dSh.

FIG. 1b shows the optical density of *S. cerevisiae* grown in minimal media in presence of a control, glyphosate (590 µM) and 7dSh (50 µM) for 48 h (initial $OD_{600}$=0.05). Values represent the mean values of three biological replicates.

This clearly shows that the activity of the compounds according to the present invention against fungi is largely higher than the activity of glyphosate.

Activity Against Plants

Suppressive Effects of 7dSh on *A. thaliana*

For a simultaneous growth, seeds of *A. thaliana* were stored at 4° C. overnight prior to initiation of germination. Seeds were germinated on solid Murashige and Skoog Basal Medium (BM) (Sigma Aldrich) (1.5% (w/v) agar) at constant illumination (60 µE) and 24° C. 7dSh and glyphosate were added to the lukewarm agar before. In order to achieve a growth of the seedlings along the agar, the plates were mounted vertically and illuminated from above.

After 7 days of germination, photographs were taken (Axioskop 2 with coupled device camera Axio Cam; Carl Zeiss) and the seedling size analyzed using Fiji software (Schindelin et al., 2012). Seedling sizes were compared by unpaired t-test using GraphPad InStat 3.

Figure 2:
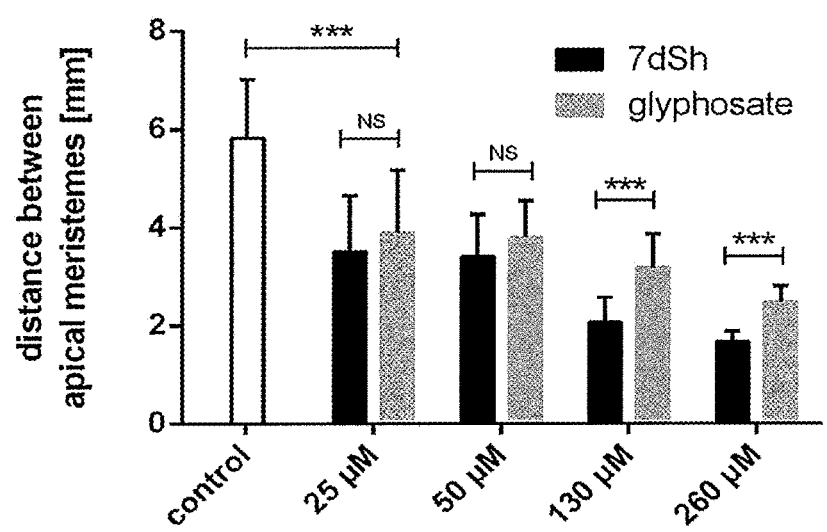
FIG. 2 shows the measurement of the distance between root and shoot apical meristem of *A. thaliana* in presence of glyphosate and 7dSh.

FIG. 2 shows the measurement of the distance between root and shoot apical meristem of *A. thaliana* in the presence of glyphosate and 7dSh. Significant differences between seedling sizes were analyzed by unpaired t-test (*P<0.01; P<0.001; *P<0.0001; NS, not significant). Values represent the mean values of at least seven biological replicates.

Significant differences were observed in the size of the seedlings: In concentrations up to 50 µM, 7dSh showed growth inhibitory effects comparable to glyphosate. In concentrations higher than 130 µM (~25 µg/mL), 7dSh exhibited a significant increased inhibitory capacity on *A. thaliana* compared to glyphosate, both in terms of seedling-size and morphological appearance. The impairment of the germination process and the morphological appearance of the seedlings was most visible in higher concentrations of 7dSh (130-260 µM). Here the germination process came to an arrest within the first days. In presence of 260 µM 7dSh the size of the seedlings (~2 mm) was three times lower compared to the control and only minor root and cotyledons formation was observed. The seedlings were impaired in gravitropism or at least did not evolve sufficiently in order to turn towards the light source. In contrast to that, equimolar glyphosate treated *A. thaliana* developed further and showed more distinct root and cotyledons formation. In presence of the inhibitors, *A. thaliana* did not undergo any morphological changes within the following 7 days.

This shows that the compounds according to the present invention clearly have a significantly stronger herbicidal effect on plants than glyphosate.

The invention claimed is:

1. A method for inhibiting enzymes involved in the shikimate pathway, comprising adding a compound to a system,
wherein the compound has a structure of formula (I)

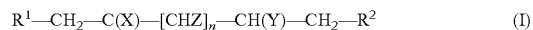

wherein
$R^1$ is OH,
$R^2$ is H, or F,
n=3,
X is O,
Y is OH,
each Z is OH,
or a cyclic form thereof,
and a stereoisomer, hydrate, salt, ester, acetal and/or tautomeric form thereof.

2. The method according to claim 1, wherein $R^2$ is H.

3. The method according to claim 1, the enzymes involved in the shikimate pathway are 3-dehydroquinate synthase.

4. A method for the inhibition of the growth of *legionella*, comprising adding a compound to a system,
wherein the compound has a structure of formula (I)

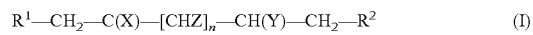

wherein
$R^1$ is OH,
$R^2$ is H, or F,
n=3,
X is O,
Y is OH,
each Z is OH,
or a cyclic form thereof,
and a stereoisomer, hydrate, salt, ester, acetal and/or tautomeric form thereof.

5. The method according to claim 4, wherein $R^2$ is H.

6. A herbicidal composition comprising a herbicide,
wherein the herbicide comprises a compound having a structure of formula (I),

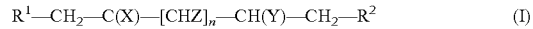

wherein
$R^1$ is OH,
$R^2$ is H, or F,
n=3,
X is O,
Y is OH,
each Z is OH,
or a cyclic form thereof,
and a stereoisomer, hydrate, salt, ester, acetal and/or tautomeric form thereof,
wherein the compound inhibits the growth of organisms having the shikimate pathway.

7. The herbicidal composition according to claim 6, wherein $R^2$ is H.

8. The herbicidal composition according to claim 6, wherein the compound is a non-selective herbicide.

9. An algicidal composition comprising an algicide,
wherein the algicide comprises a compound having a structure of formula (I),

wherein
$R^1$ is OH,
$R^2$ is H, or F,
n=3,
X is O,
Y is OH,
each Z is OH,
or a cyclic form thereof,
and a stereoisomer, hydrate, salt, ester, acetal and/or tautomeric form thereof,
wherein the compound inhibits the growth of organisms having the shikimate pathway.

10. The algicidal composition according to claim 9, wherein $R^2$ is H.

* * * * *